US00PP23364P2

(12) United States Plant Patent
Klemm et al.

(10) Patent No.: US PP23,364 P2
(45) Date of Patent: Jan. 29, 2013

(54) CARNATION PLANT NAMED 'KLEDG10119'

(50) Latin Name: *Dianthus allwoodii*
Varietal Denomination: KLEDG10119

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 46 days.

(21) Appl. No.: 13/135,740

(22) Filed: Jul. 14, 2011

(51) Int. Cl.
*A01H 5/00* (2006.01)

(52) U.S. Cl. ..... Plt./277

(58) Field of Classification Search ..... Plt./276, Plt./277, 273
See application file for complete search history.

*Primary Examiner* — Kent L Bell
(74) *Attorney, Agent, or Firm* — Jondle & Associates, P.C.

(57) ABSTRACT

A new variety of carnation named 'KLEDG10119' particularly characterized by its good indoor performance, good branching and early, rich flowering, is disclosed.

1 Drawing Sheet

Genus and species: *Dianthus allwoodii.*
Variety denomination: 'KLEDG10119'.

BACKGROUND OF THE NEW PLANT

The present invention comprises a new and distinct variety of carnation, botanically known as Dianthus allwoodii, and hereinafter referred to by the variety name 'KLEDG10119'. The new variety is the result of a cross conducted in June 2006 in Stuttgart, Germany between the proprietary female parent carnation plant, an unnamed plant of *Dianthus allwoodii* (unpatented) and the proprietary male parent, 'DCP 06 026' (unpatented). A single plant selection was subsequently chosen for further evaluation and for asexual propagation. The new variety was first propagated via vegetative cuttings in June 2007 in Stuttgart, Germany and has been asexually reproduced repeatedly by vegetative cuttings in Stuttgart, Germany for approximately six to seven generations. 'KLEDG10119' has been found to retain its distinctive characteristics through successive asexual propagations via vegetative cuttings.

Plant Breeder's Rights for this variety were applied for in Europe on Jul. 15, 2010. 'KLEDG10119' has not been made publicly available or sold more than one year prior to the filing date of this application.

SUMMARY OF THE INVENTION

The following are the most outstanding and distinguishing characteristics of this new variety when grown under normal horticultural practices in a greenhouse in Stuttgart, Germany.

1. Good indoor performance;
2. Good branching; and
3. Early, rich flowering.

DESCRIPTION OF THE PHOTOGRAPH

This new Carnation plant is illustrated by the accompanying photograph which shows the flowers and foliage of the plant. The colors shown are as true as can be reasonably obtained by conventional photographic procedures. The photograph was taken in April 2010 of a 5-month-old plant grown from rooted cuttings in a 10 centimeter pot in a glass-covered greenhouse in Stuttgart, Germany under conditions which approximate those generally used in horticultural practice.

DESCRIPTION OF THE NEW VARIETY

The following detailed descriptions set forth the distinctive characteristics of 'KLEDG10119'. The data which define these characteristics were collected from asexual reproductions carried out in Stuttgart, Germany. The plant history was taken in Spring 2010 on 5-month-old plants in 10 centimeter pots that were pinched once at week 45 and grown in a glass-covered greenhouse. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Caryophyllaceae.
- *Genus and species.*—*Dianthus allwoodii.*
- *Common name.*—Carnation.

Parentage:
- *Female parent.*—The proprietary carnation an unnamed plant of *Dianthus allwoodii* (unpatented).
- *Male parent.*—The proprietary carnation 'DCP 06 026' (unpatented).

Plant:
- *Form.*—Potted plant.
- *Habit.*—Upright, round.
- *Height (from top of soil).*—12.0 cm to 14.0 cm.
- *Width (spread).*—14.0 cm.
- *Life cycle.*—Perennial.
- *Flowering habit.*—Continuous.
- *Time to produce a finished flowering plant.*—4 months.
- *Propagation type.*—Vegetative cuttings.
- *Time to initiate roots.*—18 days.
- *Root description.*—Fine; RHS NN155C (White).
- *Temperature tolerances.*—+30° C. to −15° C.

Branches:
*Quantity per plant.*—12 to 15.
*Color.*—RHS 133B.
*Length.*—4.0 cm to 10.0 cm.
*Diameter.*—0.5 cm.
*Internode length.*—0.05 cm to 1.5 cm.
*Texture.*—Smooth.

Leaves:
*Arrangement.*—Opposite.
*Shape.*—Lanceolate.
*Apex.*—Acute.
*Base.*—Obtuse.
*Margin.*—Entire.
*Color.*—Immature leaf (both upper and lower surfaces): RHS N138B. Mature leaf (both upper and lower surfaces): RHS N138A.
*Length.*—2.0 cm to 6.0 cm.
*Width.*—0.5 cm to 0.6 cm.
*Texture.*—Smooth.
*Venation color.*—Upper surface: RHS 138A. Lower surface: RHS 138B.
*Petioles.*—Absent.

Flowers:
*Blooming habit.*—Small sprays.
*Flower type.*—Double.
*Flowering season.*—Early Spring to late Autumn.
*Width.*—3.5 cm.
*Depth.*—1.5 cm.
*Shape.*—Round.
*Fragrance.*—Present.
*Number of flowers per plant.*—6 to 8.

Flower buds:
*Color.*—RHS 137A.
*Shape.*—Elliptic.
*Length.*—1.5 cm.
*Diameter.*—0.8 cm.

Petals:
*Arrangement.*—Arranged in several whorls.
*Quantity* (*per flower*).—Greater than 18.
*Shape.*—Spoon-shaped.
*Apex.*—Obtuse.
*Margin.*—Serrate.
*Base.*—Acute.
*Length.*—1.8 cm.
*Width.*—1.5 cm.
*Color.*—When opening: Upper surface: RHS N74A. Lower surface: RHS N74B. When fully opened: Upper surface: RHS N74B and RHS 64A (at eye). Lower surface: RHS 74C.
*Texture* (*both surfaces*).—Smooth.

Sepals:
*Calyx.*—Form: Cylinder vase. Length: 1.5 cm. Width: 0.8 cm.
*Arrangement.*—Fused.
*Quantity* (*per flower*).—3 to 4.
*Shape.*—Elliptic.
*Apex.*—Acute.
*Base.*—Obtuse.
*Margin.*—Smooth.
*Length.*—0.6 cm.
*Width.*—0.5 cm.
*Color.*—Upper surface: RHS 133B and RHS 137C. Lower surface: RHS 133B and RHS 133D.
*Texture* (*both surfaces*).—Smooth.

Peduncle:
*Length.*—6.0 cm to 10.0 cm.
*Diameter.*—0.3 cm.
*Texture.*—Smooth.
*Color.*—RHS 133A.

Reproductive organs:
*Pistils.*—Quantity: 2. Stigma color: RHS 69A to RHS 69B. Ovary color: RHS 138D.
*Stamens.*—Quantity: Moderate. Filament: Length: 1.5 cm. Color: RHS 69D. Anther color: RHS 69A. Pollen: Amount: Moderate. Color: RHS 76C.

Fruit and seed set: None observed.

Disease and insect resistance: No particular resistance or susceptibility to common carnation diseases or insect pests has been observed.

COMPARISON WITH PARENTAL VARIETIES

'KLEDG10119' differs from the female parent, the proprietary Carnation plant plant, an unnamed plant of *Dianthus allwoodii* (unpatented), in that 'KLEDG10119' has double, orchid colored flowers, while the unnamed plant of *Dianthus allwoodii* has semi-double, light pink colored flowers.

'KLEDG10119' differs from the male parent, the proprietary Carnation plant 'DCP 06 026' (unpatented), in that 'KLEDG10119' has orchid colored flowers, a compact growth habit, and strong branching, while 'DCP 06 026' has lavender colored flowers, a strong growth habit and less strong branching.

We claim:

1. A new and distinct variety of carnation plant named 'KLEDG10119' as shown and described herein.

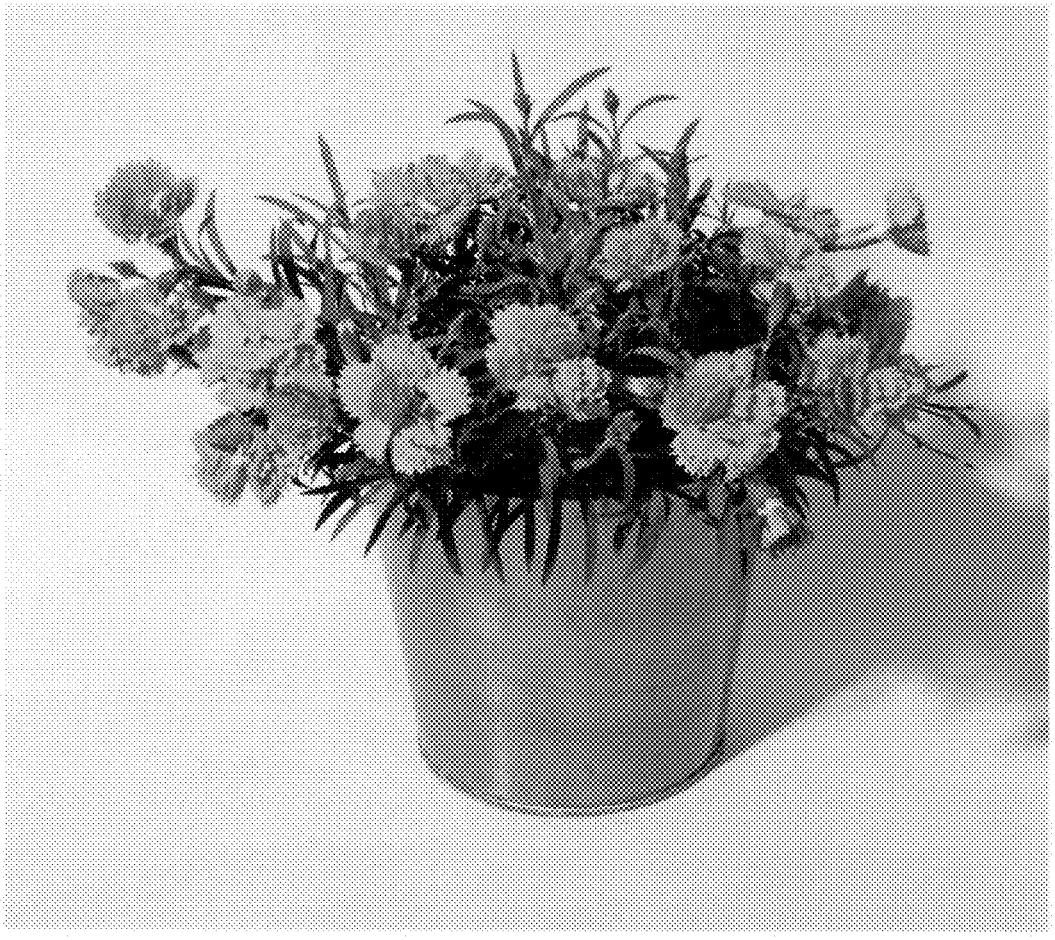

* * * * *